United States Patent [19]

Davis et al.

[11] Patent Number: 5,114,464
[45] Date of Patent: May 19, 1992

[54] 4-QUINOXALINYLOXYPHENOXYALK-YLINITRILE HERBICIDES

[75] Inventors: Robert G. Davis, Naugatuck; Allyn R. Bell, Cheshire, both of Conn.

[73] Assignee: Uniroyal Chemical Company, Inc., Middlebury, Conn.

[21] Appl. No.: 589,293

[22] Filed: Sep. 27, 1990

[51] Int. Cl.$^5$ .................... H01N 43/60; C07D 241/44
[52] U.S. Cl. ........................................ 71/92; 344/354
[58] Field of Search ........................ 71/92; 544/354

[56] References Cited

U.S. PATENT DOCUMENTS 4,609,396  12/1986  Fawzi .................................. 71/92

FOREIGN PATENT DOCUMENTS 23785    2/1981   European Pat. Off. .
42750   12/1981   European Pat. Off. .
46467    3/1982   European Pat. Off. .
0046468  3/1982   European Pat. Off. .

OTHER PUBLICATIONS

Nissan Chemical Industries, Chem. Abs. 97:92315K (1982).

Nissan Chemical Industries, Chem. Abstracts 96:6755d (1982).

Primary Examiner—John M. Ford
Assistant Examiner—F. Bernhardt
Attorney, Agent, or Firm—Glenn E. Karta

[57] ABSTRACT

Herbicidal methods utilizing compounds having the structure

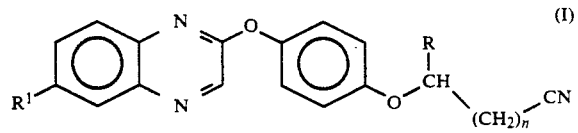

wherein:
n is 0, 1, 2, or 3;
R is H or alkyl; and
$R^1$ is halogen, nitro, methyl, halomethyl, methoxy, halomethoxy or ethoxy are disclosed which control the growth of undesirable weeds but are substantially innocuous to corn. Herbicidal compositions comprising the compounds and a carrier are also disclosed.

2 Claims, No Drawings

4-QUINOXALINYLOXYPHENOXYALKYLINITRILE HERBICIDES

BACKGROUND OF THE INVENTION

1. Field of the Invention

This invention is directed to herbicidal methods using quinoxalinyloxyphenoxyalkyl nitrile compounds which exhibit unexpectedly desirable selective herbicidal activity with high gramineous selectivity, while being relatively innocuous to corn.

Weed control is essential in the cultivation of important agronomic species such as corn, peanuts and cotton, as well as in the cultivation of many horticultural species. Moreover, the presence of such weeds on non-cropped areas may present a fire hazard, or may result in the undesirable drifting of sand or snow or irritation to persons with allergies. Accordingly, control of weeds would be beneficial, particularly in a manner which would allow for the selective control of such plants without concurrent injury to desirable crops such as corn.

2. Description of Related Art

European patent application no. 42,750 is directed to certain quinoxaline compounds disclosed as being "particularly useful for selectively removing and controlling grass weeds, including volunteer corn" (page 85, lines 12-14; emphasis added). In contrast, applicants have found that certain quinoxalinyloxyphenoxyalkyl nitrile compounds exhibit herbicidal activity against grass weeds except corn, a desirable crop.

Chemical Abstracts 96:6755d (1982) relates to certain herbicidal quinoxalines which are said to cause no damage to cotton or soybean at 5-10 kg/ha by foliar application.

E.P. 46,467 is directed to certain quinoxaline derivatives which are said to give greater than 90% control of barnyard grass when applied pre-emergently at 25 grams per acre. European patent application no. 23,785 is directed to various quinoxalines which are said to be selective herbicides against monocotyledonous plants.

SUMMARY OF THE INVENTION

This invention relates to a method of controlling undesirable gramineous weeds, while being relatively innocuous to corn. The method comprises applying to a locus to be protected an herbicidally effective amount of a compound of the formula:

(I)

wherein:
n is 0, 1, 2 or 3;
R is H or alkyl; and
$R^1$ is halogen, nitro, methyl, halomethyl, methoxy, halomethoxy or ethoxy.

DETAILED DESCRIPTION OF THE INVENTION

The compounds of formula (I) may be prepared by reacting a substituted alkylnitrile of the formula $$A-\overset{R}{\underset{|}{CH}}-(CH_2)_n-CN$$

wherein R and n are as defined above, and A can be halogen, mesylate, tosylate or other aryl sulfonates, with a quinoxalinyloxyphenol of the formula wherein $R^1$ is as defined above. The reaction is typically conducted in nonaqueous solution in the presence of an inorganic base (such as sodium carbonate, potassium carbonate or potassium hydroxide) at suitable temperature.

According to the present process, the compounds may be applied in the form of agriculturally effective compositions. The compositions are comprised of (a) an herbicidally effective amount of a compound of formula (I) as an active ingredient, and (b) an agriculturally acceptable carrier Such compositions may comprise one or more active compounds To prepare the compositions, the active compound may be mixed with an adjuvant to provide compositions in the form of finely-divided particulate solids, granules, pellets, wettable powders, flowable liquids, soluble powders, solutions, and aqueous or organic solvent dispersions or emulsions. Such formulations may be of several different physical and chemical types, and of which could be made by one familiar with the art. For instance, the agriculturally active compound may be impregnated on finely-divided or granular inorganic or organic carriers such as appapulgite clay, sand, vermiculite, corn cob, activated carbon or other granular carriers known to the art. The impregnated granules may then be spread on the soil or incorporated into the soil.

Alternatively, the chemical may be formulated as a wettable powder by grinding it into a fine powder and mixing it with an inactive powdered carrier to which a surface active dispersing agent has been added. Typical powdered solid carriers are the various mineral silicates (such as mica, talc, pyrophyllite, clays and the like) or powdered organic materials (e.g., corn cob). The wettable powder may then be dispersed in water and sprayed on the soil surface, or on crop or weed plants.

Similarly, an emulsifiable concentrate may be prepared by dissolving the chemical in a solvent such as naphtha, toluene, or other aromatic or aliphatic hydrocarbon to which a surface active dispersing agent generally has been added The emulsifiable concentrate may then be dispersed in water and applied by spraying.

The concentration of active chemical in the composition may vary widely typically ranging from about 1% to about 95% by weight. The concentration of active chemical in dispersions applied to the soil or foliage is typically between about 0.002% and about 80% by weight.

Formulations containing the active ingredient(s) may be dispersed in water or an organic liquid (such as oil) and applied to target plants. Surface active agents may be added to the applied solution to increase its qualitative or quantitive range of activity. Suitable surface active agents are well known to those skilled in the art.

Reference may be made to McCutcheon's Detergents and Emulsifiers (1980, Allured Publ. Co., Ridgewood, N.J.) for examples of appropriate surface active agents. Similarly, such formulations may be applied to the soil either as a liquid or a granule.

For use as a preemergence herbicide the active compounds are typically applied at a rate of from about 0.01 to about 10 pounds per acre (about 0.01 to about 11 kg/ha) to soil which contains weed and crop seed. Such application is made either to the surface of the soil or into the upper one to three inches (2.5 to 7.5 cm.) of soil. When employed as a postemergence herbicide, the compounds are typically applied at a rate of from about 0.01 to about 10 pounds per acre (about 0.01 to about 11 kg/ha) to the aerial portions of weeds.

The most suitable rate of application in any given case may depend on such factors as soil type, soil pH, soil organic matter content, the quantity and intensity of rainfall before and after treatment, the air and soil temperature, light intensity and light duration per day. All of these factors can have an influence on the efficacy of the chemicals for a given weed control use. However, one skilled in the art can, by routine experimentation, readily determine optimum conditions for employment of any particular compound.

It is particularly important in the practice of the present invention that the compounds be applied during the natural corn growing season, i.e., conditions of sunlight intensity, day length and temperature typically found in the so-called "corn belt" states, for example Iowa or Illinois, during May or June. It has been found that when applied for postemergent use under artificial light in a controlled environment chamber, the present compounds generally do not exhibit selectivity and tend to cause substantial injury to corn crops. Particularly good selectivity is present when the compounds are used under greenhouse conditions of natural sunlight of more than 11-12 hours per day, or in the field with natural sunlight of more than 10-11 hours per day.

The herbicidal use may include control of vegetation at industrial sites or selective weed control in crop fields.

EXAMPLES

The following Examples are intended to further illustrate the invention and are not intended to limit the scope of the invention in any manner whatsoever.

EXAMPLE 1

Preparation of
2-[4-(6-chloro-2-quinoxalinyloxy)phenoxy]acetonitrile
(Compound No. 1)

STEP 1: 2-(4-hvdroxyphenoxv)-6-chloroouinoxaline

To a one liter three-necked flask equipped with mechanical stirrer, thermometer, and connecting tube were added 29.0929 grams (0.1462 mol) of 2,6-dichloroquinoxaline, 58.1404 grams (0.5280 mol) of hydroquinone, and a solution of 28.3859 grams (0.5059 mol) of potassium hydroxide in 400 milliliters of water. The mixture was heated at 88° C. for 2.5 hours, cooled to 40° C., and 300 milliliters of water added. The slurry was filtered on a Buchner funnel, and the solid washed with water until a clear filtrate was achieved The product was dried under vacuum for 20 hours, resulting in 36.5000 grams of 2-(4-hydroxyphenoxy)-6-chloroquinoxaline, a 92% yield.

STEP 2:
2-[4-(6-chloro-2-quinoxalinyloxy)phenoxy]acetonitrile
(Compound No. 1)

To a 100 milliliter roundbottom flask equipped with reflux condenser, connecting tube, stir bar, and nitrogen atmosphere were added 2.0000 grams ($7.334 \times 10^{-3}$ mol) of 2-(4-hydroxyphenoxy)-6-chloroquinoxaline, 0.8797 grams ($7.3343 \times 10^{-3}$ mol) of bromoacetonitrile, 2.0272 grams (0.0147 mole) of anhydrous potassium carbonate, and 40 milliliters of acetonitrile. The mixture was refluxed for 20 hours, filtered hot through a Buchner funnel, and the acetonitrile removed by rotary evaporation. The combined residue of solvent removal and dichloromethane washings of potassium carbonate were plug filtered through a column of alumina with 150 milliliters of dichlormethane. Removal of dichloromethane by rotary evaporation resulted in 1.8291 grams of white solid 2-[4-(6-chloro-2-quinoxalinyloxy)phenoxy]acetonitrile (melting point 145°-146.5° C.), an 80% yield.

NMR and IR spectra of the final products and intermediates, were consistent with theoretical values. The NMR spectrum ($CDCl_3$) was as follows: 4.81(s,2H), 7.08(d,2H), 7.28(d,2H), 7.64(m,2H), 8.50(s,1H), 68(s,1H). (Note: s=singlet, d=doublet, t=triplet, q=quartet and m=multiplet.)

EXAMPLE 2

Preparation of
2-[4-(6-chloro-2-quinoxalinyloxy)phenoxy]-propionitrile (Compound No. 2)

2-[4-(6-chloro-2-quinoxalinyloxy)phenoxy]propionitrile (Compound No. 2) was prepared essentially according to the scheme set forth in Example 1, except that 1.9695 grams of 2-bromopropionitrile were substituted for the bromoacetonitrile. 3.6921 grams of product (melting point 126°-128° C.) were obtained, a 77% yield. The NMR spectrum (CDClhd 3) was as follows: 1.83(d,3H), 4.92(q,1H), 7.08-7.28(q,4H), 7.63(m,2H), 8.05(s,1H), 8.69(s,1H).

EXAMPLE 3

Preemergence Control

To illustrate the effectiveness of the Compounds 1 and 2 of this invention as preemergence herbicides, 300 mg of each compound were dissolved in 10 ml acetone to which 30 mg of an emulsifying agent, ethoxylated sorbitan monolaurate, were added. The solution was diluted to 100 ml with distilled water. Ten milliliters of the 3000 ppm solution were diluted to 250 ppm with distilled water. The chemical was applied at the rate of 10 lb/A (11.2 kg/ha) by drenching 46 ml of the 250 ppm solution on the surface of soil in 4½ inch (11.25 cm) plastic pots wherein seeds of the following weeds had been planted: velvet leaf (*Abutilon theoohrasti* Medic.) (VL), prickly sida (*sida soinosa* L.) (PS), tall morningglory (*Ioomea purourea* L. Roth) (TM), switchgrass (*Panicum viroatum* L.) (SG), barnyard grass (*Echinolchloa crusoalli* (L.) Beauv.) (BG), and green foxtail (*Setaria viridis*) (L.) Beauv.) (GF). The percent control of the weeds compared to untreated checks was determined two weeks after treatment. The results of such testing are summarized in Table I. The data presented indicates the good to excellent herbicidal efficacy exhibited by the compounds.

TABLE I

| Compound | Preemergence Activity (% Control at 11.2 kg/ha) | | | | | |
|---|---|---|---|---|---|---|
| | VL | PS | TM | BG | SG | GF |
| 1 | 0 | 0 | 0 | 100 | 50 | 90 |
| 2 | 0 | 0 | 0 | 50 | 100 | 25 |

EXAMPLE 4

Postemergence Control

To test the effectiveness of Compounds 1 and 2 of this invention as postemergence herbicides, a 3000 ppm solution of each compound (produced in accordance with the process described under Example 3) was atomized employing a DEVILBISS [trademark] sprayer, wetting the foliage to the drip point. The remainder of the procedure was the same as described under Example 3. The weeds, which were the same species as described under Example 3, were treated six days after emergence. The percent weed control was evaluated two weeks after treatment. The results of such testing are summarized in Table II.

TABLE II

| Compound | Postemergence Activity (% Control at 3000 ppm) | | | | | |
|---|---|---|---|---|---|---|
| | VL | PS | TM | BG | SG | GF |
| 1 | 0 | 0 | 0 | 100 | 100 | 9 |
| 2 | 95 | 75 | 55 | 65 | 35 | 95 |

The above data demonstrate the desirable postemergent herbicidal control exhibited by Compounds 1 and 2.

EXAMPLE 5

Postemergence Selectivity

To illustrate the effectiveness of Compound 1 of this invention as a corn-safe selective postemergence herbicide, the 3000 ppm solution prepared as described in Example 3 was diluted with distilled water to 250 ppm and applied to foliage as described in Example 3. The commercial product Hoelon 3EC® (Hoechst) was included as a standard. The foliage included weedy grasses described in Example 3 in addition to the crops corn, soybeans and cotton. The foliage was planted in a Connecticut greenhouse on May 16, and was treated on May 26. The percent weed control and crop injury was determined on Jun. 12. The results are set forth in Table III, and establish the desirable selectivity of Compound 1 as it gives good control of several grass weeds but is substantially innocuous to corn at the dose rates tested.

TABLE III

| COMPOUND | PERCENT WEED CONTROL OR CROP INJURY | | | | | |
|---|---|---|---|---|---|---|
| | SG | BG | GF | CORN | SOYBEAN | COTTON |
| 1 | 100 | 100 | 90 | 0 | 0 | 0 |
| HOELON 3EC* | 100 | 100 | 60 | 100 | 0 | 0 |

*2,4-dichlorophenoxyphenoxy acetic acid

EXAMPLE 6

Postemergence Selectivity

To further illustrate the effectiveness of Compound 1 of this invention as a corn-safe selective postemergence herbicide, field tests were run in which five corn hybrids (designated C9979, C6114, C8004 and C1914 by the Independent Professional Seedsmans Association, and Pioneer 3295) along with two grass weeds (Giant foxtail, "GF"; and Barnyard grass, "BG") were planted in an Illinois field on April 24. The crops were treated with various amounts of Compound 1 in early Jun., and the amount of crop control was evaluated 33 days after treatment compared to an untreated control. The active ingredient was formulated as follows:

| | |
|---|---|
| Compound 1 (90% active) | 11.25% by weight |
| Solvent (Exxon AROMATIC 150) | 38.75% by weight |
| Solvent (1-methyl-2-pyrollidinone) | 40% by weight |
| Emulsifier (Witco SPONTO N500B) | 10% by weight |

That produces a formulation containing 10% active ingredient by weight. The required amount of formulation to produce the indicated rate per acre is added to water, mixed with one quart of an adjuvant containing 83% mineral oil and 17% emulsifiers, then brought up to a total spray volume of 20 gallons per acre with water.

The results are set forth in Table IV, and establish the desirable selectivity of Compound 1 as it gives good control of several grass weeds but is substantially innocuous to corn at the dose rates tested.

TABLE IV

| Rate lb/a | Percent Weed Control | | | | | | |
|---|---|---|---|---|---|---|---|
| | GF | BG | 3295 | C9979 | C6114 | C8004 | C1914 |
| 0.50 | 100 | 90.0 | 0 | 0 | 0 | 0 | 0 |
| 0.25 | 100 | 43.3 | 0 | 0 | 0 | 0 | 0 |
| 0.125 | 99.3 | 30.0 | 0 | 0 | 0 | 0 | 0 |

EXAMPLE 7

Postemergence Selectivity

To illustrate the effectiveness of Compound 2 of this invention as a corn-safe selective postemergence herbicide, various concentrations of the compound were prepared and applied as in Example 5 to the following weeds and crops: velvet leaf (*Abutilon theoohrasti* Medic.) (VL), prickly sida (*Sida spinosa* L.) (PS), wild morningglory (*Ipomopa* sp.) (WM), barnyard grass (*Echinolchloa crus-galli* (L.) Beauv.) (BG), green foxtail (*Setaria viridis*) (L.) Beauv.) (GF), wild oat (*Avena fatua* L.) (WO), corn (CR), soybean (SO), cotton (CT) and rice (RC). The weeds and crops were planted in mid-September in a Connecticut greenhouse and were treated eight days later. The percent weed control and crop injury was determined 2 weeks after treatment. The results are set forth in Table IV, and establish the desirable selectivity of Compound 2 as it gives good control of several grass weeds but is substantially innocuous to corn at the dose rates tested.

TABLE V

| Rate ppm | Percent Weed Control | | | | | | | | | |
|---|---|---|---|---|---|---|---|---|---|---|
| | VL | PS | WM | WO | GF | BG | CR | SO | CT | RC |
| 3000 | 90 | 0 | 20 | 10 | 100 | 95 | 0 | 20 | 20 | 50 |

TABLE V-continued

| Rate | Percent Weed Control | | | | | | | | | |
|---|---|---|---|---|---|---|---|---|---|---|
| ppm | VL | PS | WM | WO | GF | BG | CR | SO | CT | RC |
| 2000 | 90 | 0 | 10 | 0 | 100 | 85 | 0 | 20 | 20 | 50 |
| 1000 | 90 | 0 | 10 | 0 | 100 | 85 | 0 | 20 | 20 | 50 |

We claim:

1. A method for selectively controlling the growth of undesirable gramineous plants comprising applying to the locus of such plants an herbicidally effective amount of a compound of the formula:

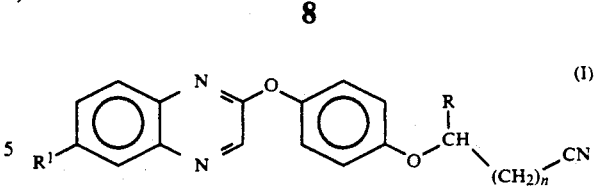

wherein:
n is 0
R is H; and
R$^1$ is halogen,
said method being substantially innocuous to corn.

2. The method of claim 1 wherein n is 0, R is H, and R$^1$ is chlorine.

* * * * *